US006554870B1

(12) United States Patent
Cotteret et al.

(10) Patent No.: US 6,554,870 B1
(45) Date of Patent: *Apr. 29, 2003

(54) COMPOSITION FOR THE OXIDATION DYEING OF KERATIN FIBRES COMPRISING A PARA-PHENYLENEDIAMINE DERIVATIVE AND A CATIONIC OR AMPHOTERIC SUBSTANTIVE POLYMER, AND THE USE THEREOF

(75) Inventors: Jean Cotteret, Verneuil sur Seine (FR); Marie-Pascale Audousset, Asnieres (FR)

(73) Assignee: L'Oreal, Paris (FR)

( * ) Notice: Subject to any disclaimer, the term of this patent is extended or adjusted under 35 U.S.C. 154(b) by 40 days.

This patent is subject to a terminal disclaimer.

(21) Appl. No.: 09/604,330

(22) Filed: Jun. 27, 2000

Related U.S. Application Data

(63) Continuation of application No. 09/235,741, filed on Jan. 20, 1999, now abandoned, which is a continuation of application No. 08/997,096, filed on Dec. 23, 1997, now abandoned, which is a division of application No. 08/686,508, filed on Jul. 26, 1996, now Pat. No. 5,735,908, which is a continuation of application No. 08/406,418, filed on Mar. 20, 1995, now abandoned.

(30) Foreign Application Priority Data

Mar. 21, 1994 (FR) ............................................ 94 03272

(51) Int. Cl.$^7$ ................................................. A61K 7/13
(52) U.S. Cl. ....................... 8/405; 8/406; 8/408; 8/410; 8/416; 8/435; 8/334; 8/555
(58) Field of Search ............................ 8/405, 406, 408, 8/410, 416, 435, 552, 334, 554, 555

(56) References Cited

U.S. PATENT DOCUMENTS

| 4,556,875 A | 12/1985 | Grollier et al. ................ 8/406 |
| 4,840,639 A | 6/1989 | Husemeyer et al. ........... 8/410 |
| 5,143,518 A | 9/1992 | Madrange et al. ............. 8/405 |
| 5,393,305 A | 2/1995 | Cohen et al. .................. 8/406 |

FOREIGN PATENT DOCUMENTS

| EP | 0 007 537 | 2/1980 |
| EP | 0 400 330 | 12/1990 |
| EP | 0 557 203 | 8/1993 |
| GB | 2 339 265 | 6/1991 |

OTHER PUBLICATIONS

ASTM Designation: D 1535—95b, "Standard Practice for Specifying Color by Munsell System," pp. 1–3.

*Primary Examiner*—Yogendra N. Gupta
*Assistant Examiner*—Eisa Elhilo
(74) *Attorney, Agent, or Firm*—Finnegan, Henderson, Farabow, Garrett & Dunner, L.L.P.

(57) ABSTRACT

The invention relates to an oxidation dye composition for keratin fibres, in particular for human keratin fibres such as hair, of the type comprising, in a medium which is suitable for dyeing, at least one oxidation dye precursor and optionally one or more couplers, and which is characterized in that it contains (i) as oxidation dye precursor, at least one para-phenylenediamine substituted in the 2-position on the benzene ring with a $C_1$–$C_4$ hydroxyalkyl or hydroxyalkoxy radical, and/or at least one of the addition salts thereof with an acid, and (ii) at least one cationic or amphoteric substantive polymer. The invention also relates to the use of this composition for dyeing keratin fibres, especially hair.

36 Claims, No Drawings

COMPOSITION FOR THE OXIDATION DYEING OF KERATIN FIBRES COMPRISING A PARA-PHENYLENEDIAMINE DERIVATIVE AND A CATIONIC OR AMPHOTERIC SUBSTANTIVE POLYMER, AND THE USE THEREOF

This is a continuation of application Ser. No. 09/235,741, filed Jan. 20, 1999, now abandoned, which is a continuation of U.S. application Ser. No. 08/997,096, filed Dec. 23, 1997, now abandoned, which is a division of U.S. application Ser. No. 08/686,508, filed Jul. 26, 1996, now U.S. Pat. No. 5,735,908, which is a continuation application of U.S. application Ser. No. 08/406,418, filed Mar. 20, 1995, now abandoned, all of which are incorporated herein by reference.

The present invention relates to a composition for the oxidation dyeing of keratin fibres and in particular of human keratin fibres, comprising at least one specific para-phenylenediamine which is substituted in the 2-position on the benzene ring, and at least one cationic or amphoteric substantive polymer. The invention also relates to the use of such a composition in cosmetic applications.

It is known to dye keratin fibres, and in particular human hair, with dye compositions containing oxidation dye precursors, in particular ortho- or para-phenylenediamines, ortho- or para-aminophenols, generally referred to as "oxidation bases", and couplers, also referred to as coloration modifiers, more particularly meta-phenylenediamine, metaminophenols and meta-diphenols, which allow the "foundation" colorations obtained with the products of condensation of the oxidation bases to be modified and enriched with glints.

It is thus especially known to dye hair with dye compositions which contain, as oxidation dye precursors, para-phenylenediamine of the type 1-hydroxyalkyl-2,5-diaminobenzene or alternatively of the type 1-hydroxyalkoxy-2,5-diaminobenzene, these precursors being combined, if required, with one or more common couplers. Such compositions are described, for example, in WO Patent Application 80/00214 and in European Patent EP-B-0,400,330, the disclosures of which are incorporated herein by reference.

However, it appeared to the Inventors that, in order to be even more satisfactory, the above dyes needed to be less selective, that is to say that they needed to be less sensitive, in dyeing terms, to the various degrees of sensitization of the hair to be dyed, in order for the colour range observed on this more or less sensitized hair to be as narrow as possible, and thus in order for the hair to be dyed uniformly. It furthermore appeared important for these compositions to be able to generate dyes whose power, on the one hand, and whose simultaneous resistance to atmospheric agents (light, bad weather), to perspiration and to the various cosmetic treatments to which the hair may be subjected (washing, permanent-waving and the like), on the other hand, is further enhanced.

Now, after considerable research conducted in this matter, it has been discovered that it is possible to obtain oxidation dyes based on compounds of the 1-hydroxyalkyl- or 1-hydroxyalkoxy-2,5-diaminobenzene type, these dyes exhibiting a markedly enhanced selectivity compared with those known hitherto, when a cationic or amphoteric substantive polymer is combined with the above compounds.

It has also been discovered that the dyes obtained using these novel compositions are more intense, while at the same time remaining very resistant to atmospheric agents and to the various above mentioned cosmetic treatments.

These discoveries form the basis of the present invention. The subject of the present invention is thus an oxidation dye composition for keratin fibres, in particular for human keratin fibres such as hair, comprising, in a medium appropriate for dyeing, at least one oxidation dye precursor (oxidation base), and if required, at least one coupler, and at least one cationic or amphoteric substantive coupler; the at least one oxidation dye precursor being selected from para-phenylenediamines of formula (I):

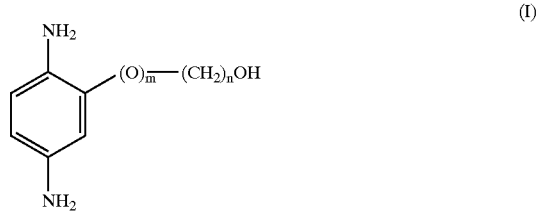

(I)

in which m is an integer equal to zero or 1, and n is an integer ranging from 1 to 4, or an acid addition salt thereof.

According to the invention, the oxidation dye precursors of formula (I) above are preferably used in combination with one or more couplers.

The new dyes obtained in the context of the present invention make it possible to achieve intense, fast and uniform colorations from the root to the tip of the hairs.

Another subject of the present invention concerns a ready-to-use composition for dyeing keratin fibres, in particular human keratin fibres such as hair, which contains at least one para-phenylenediamine of formula (I) above, at least one cationic or amphoteric substantive polymer, one or more optional couplers and at least one oxidizing agent.

The invention is also aimed at a process for dyeing keratin fibres, and in particular human keratin fibres such as hair, comprising the steps of: (i) applying to the fibres the dye composition (A1), which comprises, in a medium appropriate for dyeing, at least one para-phenylenediamine of formula (I), as described above, as an oxidation dye precursor, and one or more optional couplers, in combination with at least one cationic or amphoteric substantive polymer; and (ii) using an oxidizing agent, the oxidizing agent being applied to the fibres simultaneously with or subsequently to the dye composition, to develop the colour of the dye composition in an acidic, neutral or alkaline medium. In accordance with this embodiment of the present invention, the oxidizing agent can be mixed with the dye composition (A1) at the time of application of the dye composition to the fibres, or can be separately contained in a composition (B1) that is separately applied to the fibres simultaneously with the dye composition, or is separately applied to the fibres subsequently to the application of the dye composition.

The invention is also aimed at a variant of this process, which comprises the steps of: (i) applying to the fibres a dye composition (A2), which comprises, in a medium appropriate for dyeing, at least one para-phenylenediamine of formula (I), as described above; and (ii) applying an oxidizing composition (B2), which comprises an oxidizing agent and at least one cationic or amphoteric substantive polymer, to the fibres simultaneously with or subsequently to the dye composition, to develop the colour of the dye composition in an alkaline, neutral or acidic medium. In accordance with this embodiment of the present invention, the dye composition may further comprise at least one coupler and/or a cationic or amphoteric substantive polymer. Also in accordance with this embodiment of the present invention, the oxidizing composition (B2) can be added to the dye composition (A2) at the time of the application of the dye composition to the fibres or can be separately applied to the fibres simultaneously with or subsequently to the dye composition.

A further subject of the present invention is multi-compartment dyeing devices or "kits", a first compartment of which contains a dye composition comprising at least one para-phenylenediamine of formula (I), as described above, as an oxidation dye precursor, one or more optional couplers and at least one cationic or amphoteric substantive polymer, and a second compartment of which contains an oxidizing agent.

According to another variant, a further subject of the invention is multi-compartment dyeing devices or "kits", a first compartment of which contains a dye composition comprising at least one para-phenylenediamine of formula (I), as described above, as an oxidation dye precursor, and one or more optional couplers, in the presence or absence of a cationic or amphoteric substantive polymer, and a second compartment of which contains an oxidizing composition which comprises an oxidizing agent and at least one cationic or amphoteric substantive polymer.

However, other characteristics, aspects, objectives and advantages of the invention will emerge even more clearly upon reading the description and the examples which follow.

The para-phenylenediamine acid salts of formula (I) which may be used according to the invention are preferably chosen from the hydrochlorides, the sulphates, the hydrobromides and the tartrates.

Among the oxidation dye precursors of formula (I) which may be used in the context of the present invention, it is preferred to use 2-(β-hydroxyethyl)-para-phenylenediamine and 2-(β-hydroxyethyloxy)-para-phenylenediamine.

The concentration of this (these) precursor(s) or of the salts thereof may preferably range approximately from 0.05 to 10% by weight relative to the total weight of the dye composition applied to the hair, and more preferably range approximately from 0.1 to 5% by weight.

As defined herein, the cationic or amphoteric substantive polymer refers to a polymer with the ability to be deposited on keratin fibres, in particular human keratin fibres such as hair, as determined conventionally using the test described by Richard J. Crawford, Journal of the Society of Cosmetic Chemists, 1980, 31-(5), pages 273 to 278 (development by Red 80 acidic dye), the disclosure of which is incorporated herein by reference.

These cationic or amphoteric substantive polymers may be chosen from those previously described in the literature, in particular in European Patent Application EP-A-0,557, 203, from page 4 line 19 to page 12 line 14, the disclosure of which is incorporated herein by reference.

Other quaternized cellulose ether derivatives may also be mentioned, such as those described in European Application EP-A-0,189,935, the disclosure of which is incorporated herein by reference, and in particular the polymer marketed under the name "Quatrisoft LM 200" by the Union Carbide company; these polymers are also defined in the CTFA dictionary (5th edition, 1993) as hydroxyethylcellulose quaternary ammoniums which have been reacted with an epoxide substituted with a lauryl-dimethylammonium group and are listed therein under the name "Polyquaternium 24".

It is also possible to mention the products referred to in the CTFA dictionary (5th edition, 1993) as "Polyquaternium 37", "Polyquaternium 32", and "Polyquaternium 35", which correspond respectively, as regards "Polyquaternium 37", to crosslinked poly(methacryloyloxyethyltrimethylammonium chloride), as a 50% dispersion in mineral oil, sold under the name Salcare SC95 by the Allied Colloids company; as regards "Polyquaternium 32", to the crosslinked copolymer of acrylamide and methacryloyloxyethyltrimethylammonium chloride (20/80 by weight), as a 50% dispersion in mineral oil, sold under the name Salcare SC92 by the Allied Colloids company, and; as regards "Polyquaternium 35", to the methosulphate of the copolymer of methacryloyoxyethyl trimethylammonium and methacryloyloxyethyldimethylacetylammonium, sold under the name Plex 7525L by the Rohm GmbH company.

Among the cationic or amphoteric substantive polymers which may be used according to the invention, it is especially preferred to use:

dimethyldiallylammonium chloride homopolymer, sold under the name "Merquat 100" by the Merck company;

the copolymers of dimethyldiallylammonium chloride and acrylamide, sold under the names "Merquat 550" and "Merquat S" by the Merck company;

the quaternary polyammonium polymers prepared and described in French Patent 2,270,846, the disclosure of which is incorporated herein by reference, consisting of repeating units corresponding to the following formula (II):

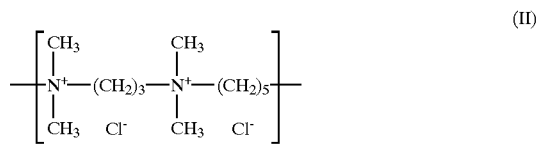

and the molecular weight of which, determined by gel permeation chromatography, ranges from 9,500 to 9,900;

the quaternary polyammonium polymers prepared and described in French Patent 2,270,846, the disclosure of which is incorporated herein by reference, consisting of repeating units corresponding to the following formula (III):

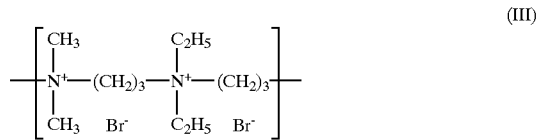

and the molecular weight of which, determined by gel permeation chromatography, is 1,200±10%, i.e., approximately ranges from 1080 to 1320;

the quaternary polyammonium polymers described and prepared in U.S. Pat. Nos. 4,157,388, 4,390,689, 4,702, 906 and 4,719,282, the disclosures of which are incorporated herein by reference, and consisting of repeating units corresponding to the following formula (IV):

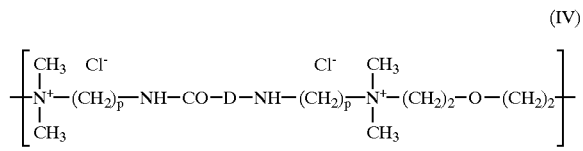

in which p represents an integer ranging approximately from 1 to 6; D may be nonexistent or may represent a group —(CH$_2$)r—CO— in which r represents a number equal to 4 or to 7, the molecular weight, determined by gel permeation chromatography, of these polymers preferably being less than 100,000, and more preferably being less than or equal to 50,000; such polymers are sold in particular by the Miranol company under the names "Mirapol A15", "Mirapol AD1", "Mirapol AZ1" and "Mirapol 175";

the copolymer of diallyldimethylammonium chloride and acrylic acid (80/20), sold under the name Merquat 280 by the Calgon company.

The concentration of the cationic or amphoteric substantive polymer may preferably range approximately from 0.02 to 10% by weight relative to the total weight of the dye composition applied to the hair, and more preferably ranges from 0.05 to 5% by weight.

The oxidizing agent is preferably chosen from hydrogen peroxide, urea peroxide, alkali metal bromates, and persalts such as perborates and persulphates. It is particularly preferred to use hydrogen peroxide.

The composition (A), which contains the combination of the dyes as described above, preferably has a pH which ranges from 3 to 11, and which may be adjusted to the desired value using basifying agents usually used in the dyeing of keratin fibres. Typical basifying agents include aqueous ammonia, alkali metal carbonates, alkanolamines, for example mono-, di- and triethanolamines as well as derivatives thereof, sodium hydroxide or potassium hydroxide, the compounds of formula:

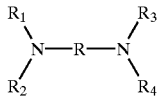

in which R is a propylene residue which is optionally substituted with a hydroxyl group or a C$_1$–C$_4$ alkyl radical; R$_1$, R$_2$, R$_3$ and R$_4$ simultaneously or independently of each other, represent a hydrogen atom, a C$_1$–C$_4$ alkyl radical or C$_1$–C$_4$ hydroxyalkyl radical. Standard acidifying agents may also be used to adjust the pH. Typical acidifying agents include inorganic or organic acids such as, for example, hydrochloric acid, tartaric acid, citric acid and phosphoric acid.

The pH of the composition (B) containing the oxidizing agent as defined above is such that, after mixing with the composition (A), the pH of the composition applied to the human keratin fibres preferably ranges from 3 to 11. The pH can be adjusted to the desired value using acidifying agents or optionally using basifying agents which are well known in the state of the art, such as those described above.

The oxidizing composition (B) preferably consists of aqueous hydrogen peroxide solution.

According to a preferred embodiment of the dyeing process of the invention, the dye composition (A) described above is mixed, at the time of use, with an oxidizing solution in a sufficient amount to develop a coloration. The mixture obtained is then applied to the human keratin fibres and is preferably left in place for 5 to 40 minutes, and more preferably for 15 to 30 minutes, after which the fibres are rinsed, washed with shampoo, rinsed again and dried.

As indicated above, the preferred dye compositions according to the invention also contain, besides the oxidation dye precursors defined above, one or more couplers.

Among these couplers, there may preferably be mentioned: 5-amino-2-methylphenol, 5-N-(β-hydroxyethyl) amino-2-methyl-phenol, 3-aminophenol, 1,3-dihydroxybenzene, 1,3-dihydroxy-2-methylbenzene, 4-chloro-1,3-dihydroxybenzene, 2,4-diamino-1-(B-hydroxyethyloxy)benzene, 2-amino-4-(β-hydroxyethylamino)-1-methoxybenzene, 1,3-diaminobenzene, 1,3-bis(2,4-diamino-phenoxy)propane, sesamol, α-naphthol, 6-hydroxyindole and 4-hydroxyindole. It is also possible to use other common couplers.

In addition to the oxidation dye precursors defined above and the optional combined couplers, the dye compositions may also contain other oxidation dye precursors as well as direct dyes, in order especially to modify the shades or to enrich the shades with glints. Their concentration by weight may preferably range approximately from 0.0005 to 10%, and may more preferably range approximately from 0.001 to 5%, relative to the total weight of the dye composition applied to the hair.

Among the additional oxidation dye precursors which may be used in the context of the present invention, there may preferably be mentioned: 4-aminophenol, 4-amino-2-methyl-phenol, 4-amino-3-methylphenol, 4-amino-2-hydroxymethylphenol, 4-amino-3-hydroxymethylphenol, para-phenylenediamine, para-tolylenediamine, 2-isopropyl-para-phenylenediamine, 2-(β-hydroxyethyloxy)-para-phenylenediamine, 1-N-bis(β-hydroxy-ethyl)amino-4-aminobenzene and 1-(β-methoxyethyl)amino-4-aminobenzene.

The direct dyes themselves may be chosen from nitro dyes, azo dyes or anthraquinone dyes.

The dye compositions may also contain antioxidants. These may be chosen in particular from sodium sulphite, thioglycolic acid, thiolactic acid, sodium bisulphite, dehydroascorbic acid, hydroquinone, 2-methylhydroquinone, tert-butylhydroquinone and homogentisic acid, and they may preferably be present in proportions ranging approximately from 0.05 to 1.5% by weight relative to the total weight of the composition.

In their preferred embodiments, the dye compositions according to the invention also contain surface-active agents which are well known in the art, in proportions approximately ranging from 0.5 to 55% by weight, and preferably from 2 to 50% by weight, relative to the total weight of the composition. Organic solvents in proportions approximately ranging from 1 to 40% by weight, and preferably from 5 to 30% by weight, relative to the total weight of the composition may also be included in the dye compositions according to the invention. The dye compositions of the invention may also contain any other cosmetically acceptable adjuvant which is known in the prior art in the oxidation dyeing of hair.

The composition applied to the hair may be provided in various forms, such as in the form of a liquid, a cream, a gel or any other form which is suitable for dyeing keratin fibres and in particular human hair. In particular, the compositions of the invention may be packaged under pressure in an aerosol can in the presence of a propellant and may form a foam.

Concrete examples illustrating the invention will now be given.

In these examples, the dyeing selectivity criterion was evaluated using the colour variation index I which was calculated according to the Nickerson equation below (see in this regard "Journal of the Optical Society of America", 1944, Sept., Vol. 34, No. 9, pp. 550–570), the disclosure of which is incorporated herein by reference:

$$I=0.4Co\Delta H+6\Delta V+3\Delta C$$

in which the parameters H, V and C represent the parameters of the Munsell notation (ASTM Standard D 1535-68) which defines the colour (H denoting the shade or Hue, V denoting the intensity or Value, and Co denoting the purity or Chromaticity of the lock relative to which it is desired to evaluate the variation in colour).

EXAMPLE 1

The following dye composition, in accordance with the invention, was prepared:

2-(β-Hydroxyethyl)-para-phenylenediamine dihydrochloride 0.675 g

5-N-(β-Hydroxyethyl)amino-2-methylphenol 0.501 g

Octyldodecanol sold under the name Eutanol G by the Henkel company 8.0 g

Oleic acid 20.0 g

Monoethanolamine lauryl ether sulphate sold under the name Sipon LM35 by the Henkel company 3.0 g Ethyl alcohol 10.0 g Benzyl alcohol 10.0 g Cetylstearyl alcohol containing 33 mol of ethylene oxide, sold under the name Simulsol GS by the Seppic company 2.4 g Ethylenediaminetetraacetic acid 0.2 g Aqueous solution containing 60% of Active Material (A.M.) of the quaternary polyammonium polymer of formula (II) 2.2 g A.M.

Monoethanolamine 7.5 g

Linoleic acid diethanolamide sold under the name Comperlan F by the Henkel company 8.0 g Sodium metabisulphite as an aqueous solution containing 35% of A.M. 0.46 g A.M.

Fragrance, preserving agent q.s.

Aqueous ammonia containing 20% of $NH_3$ 10.2 g

Hydroquinone 0.15 g

1-Phenyl-3-methyl-5-pyrazolone 0.2 g

Demineralized water q.s. 100 g

At the time of use, this composition was mixed weight for weight with 20 volume aqueous hydrogen peroxide solution (6% by weight) of pH 3.

A mixture of pH 9.8 was obtained.

The power and selectivity criteria of dyeing associated with the composition obtained were then assessed and compared, in the following way:

Evaluation of the Power

The above mixture was applied to moderately-bleached chestnut hair for 30 minutes. After rinsing, washing with shampoo, rinsing and drying, the hair was dyed a shade which, when assigned a Munsell numerical value on a Minolta CM 2002 calorimeter, corresponded to the following value:

1.5 R 2.9/3.1.

As a comparison, a duplicate of the above mixture, which contained no quaternary polyammonium polymer (the remainder of the composition thus being the same otherwise) was applied to this same moderately-bleached chestnut hair, under the same conditions. The shade then obtained corresponded to the following value:

3.1 R 3.3/3.2.

The non-dyed moderately-bleached chestnut hair (initial state) had a shade corresponding to the following value:

1.7 Y 6.2/4.6.

When applied to these values, the Nickerson equation gave colour variation indices between dyed and non-dyed hair of:

I=61.47 for hair which was dyed using the composition in accordance with the invention I=55.82 for hair which was dyed using the comparative composition, that is to say without quaternary polyammonium polymer, which demonstrates a more considerable dyeing power with the composition according to the invention.

Evaluation of the Selectivity:

By applying the mixture in accordance with the invention prepared above, and under the same treatment conditions, but this time on grey hair containing 90% of white hairs, a Munsell shade of: 9.2 RP 3.9/2.5 was obtained, whereas on application of the duplicate mixture free of quaternary polyammonium polymer, a Munsell shade of: 10 RP 4.0/2.5 was obtained.

By again applying the mixture according to the invention prepared above, and under the same treatment conditions, but this time on intensely bleached hair, a Munsell shade of: 9.2 RP 3.3/3.3 was obtained, whereas on application of the duplicate mixture free of quaternary polyammonium polymer, a Munsell shade of: 9.8 RP 3.3/3.3 was obtained.

The variation in colour expressed by the Nickerson equation between 90% white hair and intensely bleached hair was thus equal to 3.0 in the case of the mixture prepared from the composition in accordance with the invention (that is to say the composition containing the quaternary polyammonium polymer), whereas this variation in colour was equal to 5.9 in the case of the duplicate composition (that is to say the composition without polymer).

The latter results show that after dyeing using the composition according to the invention (i.e., with substantive polymer), intensely bleached hair containing 90% of white hairs at the roots has a much more uniform coloration than that with a composition of the prior art (i.e., without substantive polymer).

EXAMPLE 2

The following dye composition, in accordance with the invention, was prepared:

2-(β-Hydroxyethyloxy)-para-phenylene-diamine dihydrochloride 0.480 g A.M.

5-N-(β-Hydroxyethyl)amino-2-methyl-phenol 0.33 g

Octyldodecanol sold under the name Eutanol G by the Henkel company 8.0 g

Oleic acid 20.0 g

Monoethanolamine lauryl ether sulphate sold under the name Sipon LM35 by the Henkel company 3.0 g Ethyl alcohol 10.0 g Benzyl alcohol 10.0 g Cetylstearyl alcohol containing 33 mol of ethylene oxide, sold under the name Simulsol GS by the Seppic company 2.4 g Ethylenediaminetetraacetic acid 0.2 g Quaternary polyammonium polymer sold in aqueous solution at a concentration of 52% of A.M. by the Miranol company under the name Mirapol A15 2.08 g A.M.

Monoethanolamine 7.5 g

Linoleic acid diethanolamide sold under the name Comperlan F by the Henkel company 8.0 g Sodium metabisulphite as an aqueous solution containing 35% of A.M. 0.46 g A.M.

Fragrance, preserving agent q.s.

Aqueous ammonia containing 20% of $NH_3$ 10.2 g

Hydroquinone 0.15 g

1-Phenyl-3-methyl-5-pyrazolone 0.2 g

Demineralized water q.s. 100 g

At the time of use, this composition was mixed weight for weight with 20 volume aqueous hydrogen peroxide solution (6% by weight) of pH 3.

A mixture of pH 9.8 was obtained.

This mixture was then applied to hair sensitized to varying degrees, for 30 minutes. After rinsing, washing with shampoo, rinsing and drying, the hair was dyed an intense shade and with little selectivity, that is to say that the dyeing was of good uniformity.

EXAMPLE 3

The following dye composition, in accordance with the invention, was prepared:

2-(β-Hydroxyethyl)-para-phenylenediamine dihydrochloride 0.450 g

5-Amino-2-methylphenol 0.250 g

Octyldodecanol sold under the name Eutanol G by the Henkel company 8.0 g

Oleic acid 20.0 g

Monoethanolamine lauryl ether sulphate sold under the name Sipon LM35 by the Henkel company 3.0 g Ethyl alcohol 10.0 g Benzyl alcohol 10.0 g Cetylstearyl alcohol containing 33 mol of ethylene oxide, sold under the name Simulsol GS by the Seppic company 2.4 g Ethylenediaminetetraacetic acid 0.2 g Dimethyldiallylammonium chloride homopolymer sold in aqueous solution at a concentration of 40% of A.M. by the Merck company under the name Merquat 100 2.0 g A.M.

Monoethanolamine 7.5 g

Linoleic acid diethanolamide sold under the name Comperlan F by the Henkel company 8.0 g Sodium metabisulphite as an aqueous solution containing 35% of A.M. 0.46 g A.M.

Fragrance, preserving agent q.s.

Aqueous ammonia containing 20% of NH3 10.2 g

Hydroquinone 0.15 g

1-Phenyl-3-methyl-5-pyrazolone 0.2 g

Demineralized water q.s. 100 g

At the time of use, this composition was mixed weight for weight with 20 volume aqueous hydrogen peroxide solution (6% by weight) of pH 3.

A mixture of pH 9.8 was obtained.

This mixture was then applied to hair sensitized to varying degrees, for 30 minutes. After rinsing, washing with shampoo, rinsing and drying, the hair was dyed an intense shade and with little selectivity, that is to say that the dyeing was of good uniformity.

EXAMPLE 4

The following dye composition, in accordance with the invention, was prepared:

2-(β-Hydroxyethyl)-para-phenylene-diamine dihydrochloride 0.337 g 2,4-Diamino-1-(β-hydroxyethyloxy)-benzene dihydrochloride 0.361 g Cetylstearyl alcohol 10.0 g Oxyethylenated oleocetyl alcohol containing 30 mol of ethylene oxide 5.0 g Sodium magnesium lauryl ether sulphate as a solution containing 26% of A.M. 2.6 g A.M.

Copolymer of dimethyldiallylammonium chloride and acrylic acid (80/20) as an aqueous solution containing 35% of A.M., sold by the Merck company under the name Merquat 280 1.75 g A.M.

Sodium metabisulphite as an aqueous solution containing 35% of A.M. 0.46 g A.M.

Fragrance, preserving agent q.s.

Diethylenetriaminepentaacetic acid containing 40% of A.M. 0.8 g A.M.

Aqueous ammonia containing 20% of $NH_3$ 10.2 g

Hydroquinone 0.15 g

1-Phenyl-3-methyl-5-pyrazolone 0.2 g

Demineralized water q.s. 100 g

At the time of use, this composition was mixed weight for weight with 20 volume aqueous hydrogen peroxide solution (6% by weight) of pH 3.

A mixture of pH 9.8 was obtained.

This mixture was then applied to hair sensitized to varying degrees, for 30 minutes. After rinsing, washing with shampoo, rinsing and drying, the hair was dyed an intense shade and with little selectivity, that is to say that the dyeing was of good uniformity.

What is claimed is:

1. An oxidation dye composition for keratin fibres, comprising, in a medium appropriate for dyeing, at least one oxidation dye precursor, at least one coupler, and at least one cationic or amphoteric substantive polymer; said at least one oxidation dye precursor being selected from para-phenylenediamines of formula (I):

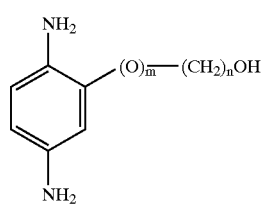

(I)

in which m is an integer equal to zero, and n is an integer ranging from 1 to 4, or an acid addition salt thereof;

and said at least one cationic or amphoteric substantive polymer, being selected from:

(i) a copolymer of dimethyldiallylammonium chloride and acrylamide;

(ii) a quaternary polyammonium polymer consisting of repeating units of formula (II):

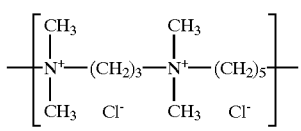

wherein said polymer has a molecular weight, determined by gel permeation chromatography, which ranges from 9500 to 9900;

(iii) a quaternary polyammonium polymer consisting of repeating units of formula (III):

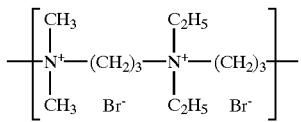

wherein said polymer has a molecular weight, determined by gel permeation chromatography, which ranges from 1080 to 1320;

(iv) a quaternary polyammonium polymer consisting of repeating units of formula (IV):

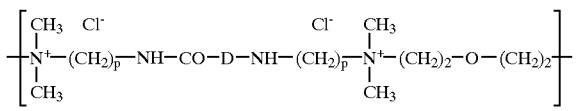

in which p represents an integer ranging from 1 to 6; D may be nonexistent or may represent a group $(CH_2)_r-CO-$ in which r represents a number equal to 4 or 7, and wherein said polymer has a molecular weight, determined by gel permeation chromatography, of less than 100,000; or (v) a copolymer of diallyldimethylammonium chloride and acrylic acid.

2. A composition according to claim 1, wherein the para-phenylenediamine of formula (I) is 2-(β-hydroxyethyl)-para-phenylenediamine or an acid addition salt thereof.

3. A composition according to claim 1, wherein said quaternary polyammonium polymer consisting of repeating units of formula (IV) has a molecular weight, determined by gel permeation chromatography, of less than or equal to 50,000.

4. A composition according to claim 1, wherein said acid addition salt of the para-phenylenediamine of formula (I) is selected from the hydrochlorides, the sulphates, the hydrobromides and the tartrates.

5. A composition according to claim 1, wherein said para-phenylenediamine of formula (I), or the salt thereof, is present in a concentration ranging from 0.05 to 10% by weight, relative to the total weight of the composition.

6. A composition according to claim 5, wherein said para-phenylenediamine of formula (I), or the salt thereof, is present in a concentration ranging from 0.1 to 5% by weight, relative to the total weight of the composition.

7. A composition according to claim 1, wherein the cationic or amphoteric substantive polymer is present in a concentration ranging from 0.02 to 10% by weight, relative to the total weight of the composition.

8. A composition according to claim 7, wherein the cationic or amphoteric substantive polymer is present in a concentration ranging from 0.05 to 5% by weight, relative to the total weight of the composition.

9. A composition according to claim 1, wherein said composition contains at least one coupler.

10. A composition according to claim 1, wherein said composition additionally contains direct dyes and/or oxidation dye precursors other than those corresponding to formula (I).

11. A composition according to claim 1, which is ready to apply and which additionally contains an oxidizing agent and has a pH ranging from 3 to 11.

12. A process for dyeing keratin fibres, comprising the steps of:
   (i) applying to said fibres the dye composition according to claim 1; and
   (ii) applying an oxidizing agent to said fibres simultaneously with or subsequently to said dye composition, to develop a colour of said dyeing composition in an acidic, neutral or alkaline medium.

13. A process according to claim 12, wherein said oxidizing agent is added to said dye composition at the time of applying in step (i).

14. A process according to claim 12, wherein said oxidizing agent is separately contained in a second composition and is separately applied to said fibres simultaneously with said dye composition.

15. A process according to claim 12, wherein said oxidizing agent is separately contained in a second composition and is separately applied to said fibres subsequently to said application of said dye composition.

16. A process according to claim 12, wherein said fibres are human keratin fibres.

17. A process for dyeing keratin fibres, comprising the steps of:
   (i) applying to said fibres a dye composition, which comprises, in a medium appropriate for dying, at least one para-phenylenediamine of formula (I):

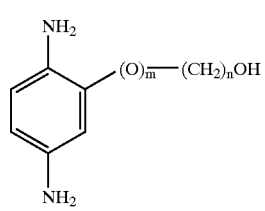

in which m is an integer equal to zero, and n is an integer ranging from 1 to 4, or an acid addition salt thereof; and
   (ii) applying an oxidizing composition, which comprises an oxidizing agent and at least one cationic or amphoteric substantive polymer, to said fibres simultaneously with or subsequently to said dye composition, to develop a colour of said dye composition in an alkaline, neutral or acidic medium.

18. A process according to claim 17, wherein said dye composition further comprises at least one coupler.

19. A process according to claim 17, wherein said dye composition further comprises a cationic or amphoteric substantive polymer.

20. A process according to claim 17, wherein said oxidizing composition is added to said dye composition at the time of applying in step (i).

21. A process according to claim 17, wherein said oxidizing composition is separately applied to said fibres simultaneously with said dye composition.

22. A process according to claim 17, wherein said oxidizing composition is separately applied to said fibres subsequent to said dye composition.

23. A process according to claim 17, wherein said fibres are human keratin fibres.

24. A kit for dyeing keratin fibres comprising at least two compartments, at least one of said compartments containing a dye composition according to claim 1, and at least one other of said compartments containing a composition comprising an oxidizing agent in a medium appropriate for dyeing.

25. A kit according to claim 24, wherein said keratin fibres are human keratin fibres.

26. A kit for dyeing keratin fibres comprising at least two compartments, at least one of said compartments containing a dye composition which comprises, in a medium appropriate for dyeing, at least one para-phenylenediamine of formula (I):

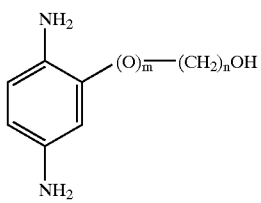

in which m is an integer equal to zero or 1, and n is an integer ranging from 1 to 4, or an acid addition salt thereof, and at least one other of said compartments containing an oxidizing composition which comprises an oxidizing agent and at least one cationic or amphoteric substantive polymer.

27. A kit according to claim 26, wherein said at least one compartment containing said dye composition further contains at least one coupler.

28. A kit according to claim 26, wherein said keratin fibres are human keratin fibres.

29. A process for dyeing keratin fibres comprising the steps of:
(i) applying to said fibres a dye composition according to claim 1, said dye composition being obtained from a kit for dyeing keratin fibres comprising at least two compartments, at least one of said compartments containing a dye composition according to claim 1, and at least one other of said compartments containing a composition comprising an oxidizing agent in a medium appropriate for dyeing; and
(ii) applying, to develop a colour of said dye composition in said medium, said oxidizing agent and said appropriate dyeing medium to said fibres simultaneously with or subsequently to the application of said dyeing composition to said fibres.

30. A process according to claim 26, wherein said keratin fibres are human keratin fibres.

31. A process for dyeing keratin fibres, comprising the steps of:
(i) applying to said fibres a dye composition, which comprises, in a medium appropriate for dying, at least one para-phenylenediamine of formula (I):

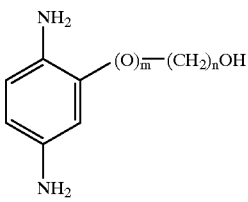

in which m is an integer equal to zero, and n is an integer ranging from 1 to 4, or an acid addition salt thereof, said dye composition being obtained from a kit for dyeing keratin fibres comprising at least two compartments, at least one of said compartments containing said dye composition, and at least one other of said compartments containing an oxidizing composition which comprises an oxidizing agent and at least one cationic or amphoteric substantive polymer; and
(ii) applying, to develop a colour of said dye composition, said oxidizing composition to said fibres simultaneously with or subsequenly to the application of said dyeing composition to said fibres.

32. A process according to claim 31, wherein said at least one compartment containing said dye composition further contains at least one coupler.

33. A process according to claim 31, wherein said keratin fibres are human keratin fibres.

34. A composition according to claim 1, wherein said keratin fibres are human keratin fibres.

35. A composition according to claim 34, wherein said human keratin fibres are hair.

36. A composition according to claim 1, which is in the form of a liquid, a cream or a gel.

* * * * *

UNITED STATES PATENT AND TRADEMARK OFFICE
CERTIFICATE OF CORRECTION

PATENT NO.    : 6,554,870 B1  
DATED         : April 29, 2003  
INVENTOR(S)   : Jean Cotteret et al.

It is certified that error appears in the above-identified patent and that said Letters Patent is hereby corrected as shown below:

<u>Title page,</u>
Item [*] Notice, should read
-- [*]   Notice:  Subject to any disclaimer, the term of this patent is extended or adjusted under 35 U.S.C. 154 (b) by 0 days. --

Signed and Sealed this

Twenty-eighth Day of October, 2003

JAMES E. ROGAN
*Director of the United States Patent and Trademark Office*